US008894945B2

(12) United States Patent
Vergara Pinto

(10) Patent No.: US 8,894,945 B2
(45) Date of Patent: Nov. 25, 2014

(54) PORTABLE STERILIZING EQUIPMENT TO LOAD TRANSPORTABLE ASEPTIC CONTAINERS

(75) Inventor: Rodrigo Vergara Pinto, Mellipilla (CL)

(73) Assignee: Andesocean S.A., Santiago (CL)

( * ) Notice: Subject to any disclaimer, the term of this patent is extended or adjusted under 35 U.S.C. 154(b) by 209 days.

(21) Appl. No.: 13/805,178

(22) PCT Filed: Jun. 7, 2011

(86) PCT No.: PCT/IB2011/052482
§ 371 (c)(1),
(2), (4) Date: Feb. 5, 2013

(87) PCT Pub. No.: WO2011/158152
PCT Pub. Date: Dec. 22, 2011

(65) Prior Publication Data
US 2013/0125510 A1 May 23, 2013

(30) Foreign Application Priority Data
Jun. 18, 2010 (CL) .................................... 644-2010

(51) Int. Cl.
*A61L 2/00* (2006.01)
(Continued)

(52) U.S. Cl.
CPC ... *A61L 2/20* (2013.01); *A61L 2/07* (2013.01);
(Continued)

(58) Field of Classification Search
CPC ............... A61L 2/00; A61L 2/07; B01B 1/00; B05C 7/00; B08B 3/04
USPC ........ 422/26, 28, 292, 298, 307, 309; 99/348, 99/275; 134/134, 25.3, 10, 34, 109, 103.1, 134/56 R, 168 R, 166 C–167 C, 169 C; 141/89, 48, 129
See application file for complete search history.

(56) References Cited

U.S. PATENT DOCUMENTS 5,680,877 A 10/1997 Edstrand et al.
6,161,558 A * 12/2000 Franks et al. ............... 134/57 R

FOREIGN PATENT DOCUMENTS

ES 2 208 062 6/2004

OTHER PUBLICATIONS

Pharmaceutical CIP Units, INEXPO, Nov. 2008—http://web.archive.org/web/20081113230326/http://www.inoxpa.com/en/product/1210/pharmaceutical-cip-units.html—4 pages.

*Primary Examiner* — Monzer R Chorbaji
(74) *Attorney, Agent, or Firm* — Hamre, Schumann, Mueller & Larson, P.C.

(57) ABSTRACT

The invention discloses a portable sterilizer for use when filling containers for transporting goods under aseptic conditions, which provides increased transport capacity, more flexible formats and connections for the containers, while facilitating handling of the goods, and which comprises a portable boiler, systems for pre-washing using chemicals and other means necessary for sanitizing all the parts thereof. For washing, it uses chemicals, circulation waters and the hot water (or any other liquid poured into said boiler) produced from the liquid phase inside said portable boiler. The device may include a pump for pressure washing with other types of cleaners, cold water, chemicals, etc.; For sterilizing, it uses the vapour phase of water or other liquids in said portable boiler, ultraviolet rays and/or another means of sterilization, and it is connected between the outlet of the pasteurization system of a production plant and the return lines of said pasteurizer. Said system is connected by means of flexible hoses. The system washes and sterilizes the filling and return lines of receptacles or containers, as well as the valve of said receptacles or containers. The system may also wash and sterilize the filling and return lines of the producer in a partial manner.

3 Claims, 1 Drawing Sheet

(51) Int. Cl.

| | |
|---|---|
| ***B08B 3/00*** | (2006.01) |
| ***B65B 1/04*** | (2006.01) |
| ***B65B 31/00*** | (2006.01) |
| ***A61L 2/20*** | (2006.01) |
| ***A61L 2/07*** | (2006.01) |
| ***A61L 2/10*** | (2006.01) |
| ***B65B 55/00*** | (2006.01) |

(52) U.S. Cl.

CPC .................. *A61L 2/10* (2013.01); *B65B 55/00* (2013.01); *A61L 2202/16* (2013.01); *A61L 2202/17* (2013.01); *A61L 2202/23* (2013.01)

USPC ........... 422/298; 422/292; 422/307; 422/309; 99/348; 134/134; 134/109; 134/103.1; 134/56 R; 134/168 R; 141/89; 141/48; 141/129

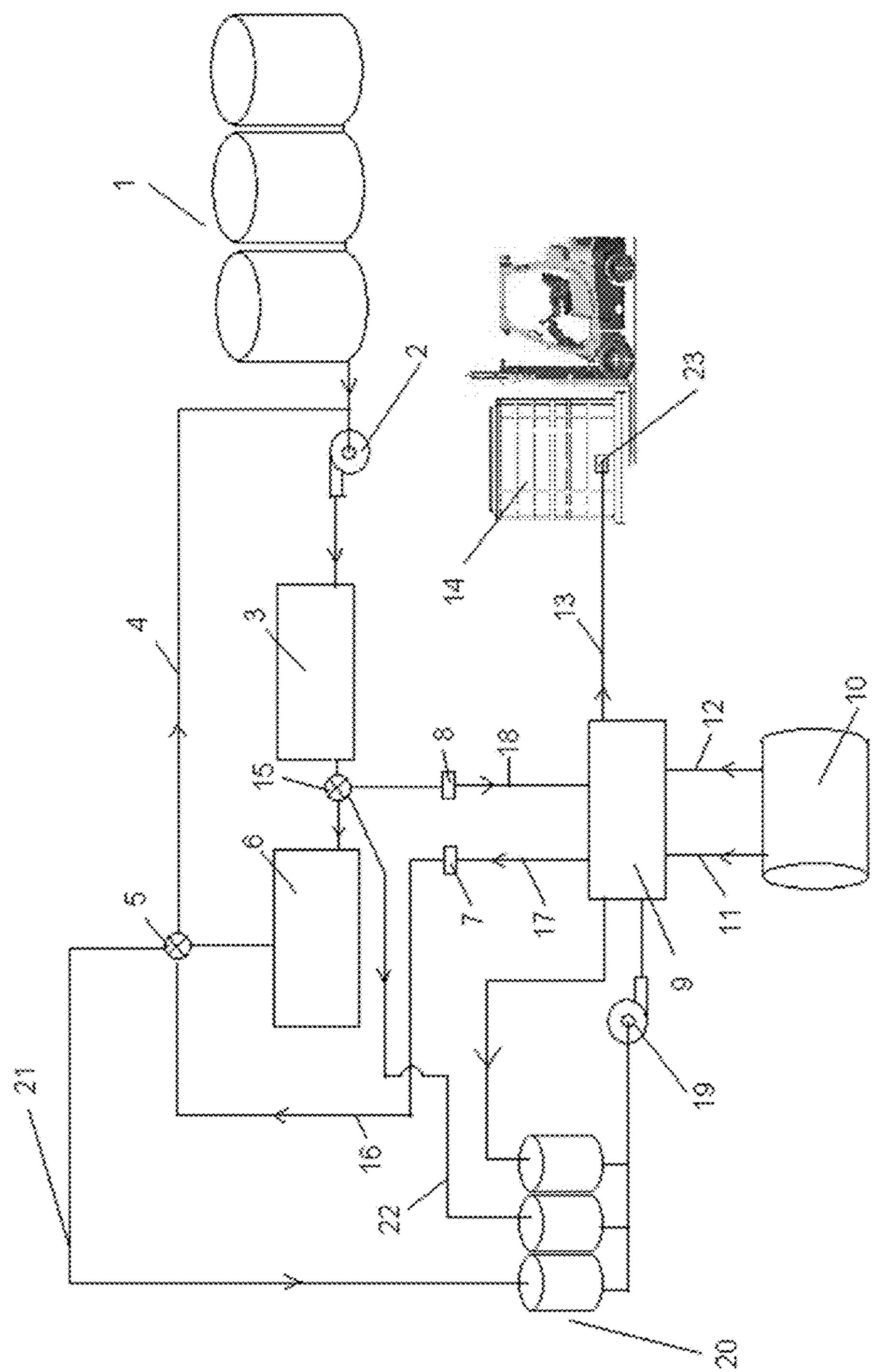

PORTABLE STERILIZING EQUIPMENT TO LOAD TRANSPORTABLE ASEPTIC CONTAINERS

FIELD OF THE INVENTION

The present invention consists in a portable sterilizing equipment to be used in loading containers for transporting products aseptically.

DESCRIPTION OF PRIOR ART

Under the current state of the art drums of 80 to 205 liters are used with a sterilized bag for the transportation of products that must be carried aseptically, which involves handling, transporting and storing a great number of these drums. Filling of these drums must be performed inside the producer's facilities to be later transferred and loaded into a means of transportation.

SUMMARY OF THE INVENTION

The present invention describes a portable, self-contained and useful machine to sterilize the necessary lines and valves for the transportation of products aseptically in containers or tanks also sterilized. It basically consists in the machine itself accompanied by a boiler or vapor generator also portable and that forms integral part of said portable machine. This machine also has prior washing systems, using chemicals and other means necessary for the washing and sanitation of all its parts.

The portable machine would perform the function of washing, sanitizing and sterilizing the area between the machine and the container and/or all pipes feeding and feeding-back said machine between the pasteurization facilities and the valves of the container. For washing purposes, chemicals are used, as well as recirculation water and the hot water resulting from the liquid phase inside the portable boiler; for sterilization the vapor phase inside this portable boiler would be used and/or other sterilization means. These other means could be ultraviolet light, radiation or any other available method. In addition, and if necessary, the machine could also sterilize part of the producer's filling and returning pipes.

The machine shall allow making the type and size of containers flexible that may be loaded aseptically; this would result in significant savings in freight, loading and unloading times for the product from the pasteurization system to the transportation means, and also savings in relation to the costs of container materials and handling necessary for the filling and transportation of them to their final destination, thus improving competitiveness of domestic products as compared with other markets that do not have this innovating alternative.

The machine would be placed between the pasteurization system's outlet from a facility located inside the producer's premises and the returning lines of said pasteurization system, temporarily replacing the fixed-format filling system existing at said facility. This machine is inserted between the pasteurization system and the existing filling system for a fixed size of container. The connection of said portable machine would be done through flexible hoses, which in turn make the size and position of the containers to be loaded aseptically flexible.

The containers or tanks for the transportation of products are mainly flexible tanks, rigid or semi-rigid tanks and any other transportation element with a capacity between 1,000 and 30,000 liters. Containers or tanks would be previously sterilized inside by using Gamma rays, ultraviolet light or another proper means for the kind of container to be filled.

BRIEF DESCRIPTION OF FIGURES

FIG. 1 shows an installation scheme.

DETAILED DESCRIPTION OF THE INVENTION

At the producer's facilities located inside the plant or warehouse, storage tanks for the product (1) are considered equipped with a pump (2) to pump the content from said tanks (1) to the pasteurizer (3) and a by-pas valve (15) is installed allowing the processed product from the pasteurizer to continue its way to the customer's packaging system (6) or said product may continue its way to the filling coupling (8), from which the product may be taken to the tank or transportation container (14). Also a returning line (4) of the product is considered for using the customer's packaging system (6) and also a returning line (16) for the installation of an external tank (14). According to the position of the by-pass valve (5), the returning content may return to the pump (2) from the customer's packaging system (6) or from the external tank (14).

For the use of the portable machine for sterilization, inserting the machine (9) and its boiler (10) at the producer's facilities is considered by connecting flexible hoses (17) and (18). For the sterilization of the tank valve or transportation container, the flexible hose (13) is used. The machine may provide washing and sterilization from the filling couplings (8) and returning couplings (7) to the producer's filling and returning lines if necessary. The fluids for washing are within tanks (20) for such purposes and they are pumped through the washing machine (9) by the pump (19) to the filling couplings (8) and returning couplings (7). Consequently, the returning lines (16) are washed and when valve (5) is closed to the filling machine (6), the fluid returns to the tanks (20) though the line (21). Also the section between the coupling (8) and the valve (15) is washed when said valve is closed to the filling machine (6), with the fluid returning to the tanks (20) through the line (22). Also the tank's inlet valve may be washed through the flexible pipe for the washing of tank (13). For washing and/or sterilization with the boiler, vapor is injected into the washing machine through the boiler's vapor outlet line (11) and the boiler's liquid phase line (12). The fluid and the vapor go through the washing machine and they are injected into the filling (8) and returning (7) couplings. Also, the tank's inlet valve may be washed through the tank's washing flexible hose (13). For washing and/or sterilization with vapor through the boiler, the washing pump is turned off.

For filling the sterilized container or tank (14), the product is by-passed through valve (15), the filling coupling (8), the flexible hose (18), through the washing machine (9) and finally through the flexible hose (13) entering through the tank's or container's valve (23) to said tank or container (14). Then said tank or container (14) is removed and sealed. If necessary, the product may be returned to the returning line through the washing machine (9), the flexible hose (17) and the coupling (7). If other tanks or containers (14) should continue to be filled, only the area between the machine and the new tank installed should be washed and sterilized, including the tank's valve (23).

The invention claimed is:

1. A portable sterilizing equipment to be used in loading containers for the transportation of products aseptically, increasing the transport capacity, making the formats and connection of containers flexible and making handling of the product easy, wherein said equipment is coupled between the pasteurization system's outlet from a producer's facility comprising tanks with fluid for washing, and a retuning coupling from the returning lines of said pasteurization system, wherein it comprises:

a) a portable boiler with water to generate a vapor phase and a liquid phase;
b) a washing machine connected to said portable boiler with a vapor line and with a line of liquid phase, where said washing machine comprises chemicals and circulation waters;
c) a by-pass valve connected to the pasteurization system, to the tank filling device, to tanks and to a filling coupling;
d) a flexible hose connected between said filling coupling and said washing machine;
e) a flexible hose connected between said returning coupling and said washing machine;
f) a flexible hose for tank washing connected to said washing machine and a tank valve from a container.

2. The sterilizing equipment of claim 1, wherein it comprises a pump for pressurized washing connected between the tanks of the pasteurization system and the washing machine.

3. A washing method through the portable sterilizing equipment of claim 1, wherein it comprises:

a. connecting the portable sterilizing equipment to the producer's filling couplings and returning couplings through flexible hoses;
b. washing said filling and returning couplings and said flexible hoses with different methods;
c. sterilizing said filling and returning couplings and said flexible hoses;
d. washing the tank valve of the transportation container or tank;
e. sterilizing said tank valve;
f. loading said container or tank;
g. washing the area between the washing machine and the container if applicable;
h. sterilizing said area between the washing machine and filling;
i. removing the tank once filled;
j. sealing said container;
k. installing a new tank if applicable;
l. sterilizing the area between the washing machine and the new container installed including the tank valve; and
m. continuing with steps d) through l) until completing the number of containers to be filled.

* * * * *